United States Patent [19]
Reichert

[11] Patent Number: 4,831,057
[45] Date of Patent: May 16, 1989

[54] ANTISNORING AGENT
[76] Inventor: Dietrich Reichert, Can d'en Pol, Sta.Eulalia d.R., Ibiza, Spain
[21] Appl. No.: 47,560
[22] Filed: Apr. 27, 1987

Related U.S. Application Data
[63] Continuation of Ser. No. 609,287, May 11, 1984, abandoned.

[30] Foreign Application Priority Data
May 13, 1983 [DE] Fed. Rep. of Germany ....... 3317530
May 13, 1983 [DE] Fed. Rep. of Germany ....... 3317558

[51] Int. Cl.$^4$ ............................................. A61K 31/13
[52] U.S. Cl. .................................................. 514/647
[58] Field of Search ........................................ 514/647

[56] References Cited
FOREIGN PATENT DOCUMENTS
2101485A 1/1983 United Kingdom .

OTHER PUBLICATIONS
A.Ph.A. (1977), Handbook of Nonprescription Drugs, pp. 184–188, Sleep Aid & Sedative, pp. 76–111, Cold and Allergy.
Reichert, C.A., 97, #98382b (1982) of EPO 53754, 16 Jun. 1982, Drug for Controlling Snoring and Its Use.
Dubon et al., C.A., 102, #190973q (1985).
Reichert, C.A., 102, #84405w, #84406x of Ger. Off. 3,317,558, & 3,317,530.
Klier et al, C.A., 88, #164474a (1978).
Chem. Abstracts, 94, #202596a, #202597b, #202598c, #202599d, #202600x (1981), Saito et al., Okamiya et al., Wada et al., Makita et al., Matsuzawa et al.
Chem Abstracts, 95, #418d, #419e, #420y (1981), Wada et al., Wada et al., Matsuzawa et al.

Primary Examiner—Shep K. Rose
Attorney, Agent, or Firm—A. Thomas S. Safford

[57] ABSTRACT
Antisnoring agent for oral or local application in the nasal/pharyngal cavities comprising an active content of a secretolytically and/or secretoproductively effective substance, as the active ingredient, together with carrier substances for diluents which are compatible with mucous membranes.

2 Claims, No Drawings

ANTISNORING AGENT

This application is a continuation of application Ser. No. 609,287, filed May 11, 1984, now abandoned.

The invention concerns an antisnoring agent for oral or for local administration in the nose/pharynx cavities.

Snoring is a phenomenon which is based on rattling breathing, which may occur with human beings when asleep. Due to the resultant disturbance to other people, numerous attempts have been made in the past to remedy this phenomenon.

It was found that the cause of snoring is obstruction or unevenness in the area of the upper respiratory tracts.During the process of breathing in and out,the air is guided via complex flow paths. Unevenness in the area of these flow paths necessarily leads to turbulence in the air flow. This results in an obstruction of breathing,which is below the consciousness threshold.The obstructions in the flow path and the turbulence caused thereby have the result that locally an underpressure(-suction) occurs. This underpressure leads to fluttering motions of soft,slack structures in the area of the airflow path.In particular there is a reciprocating movement of the soft palate caused by the named turbulences.

Although numerous investigations have been made to prevent snoring,they have not yet led to the desired success.The basis was provided by agents which were composed on the foundation of chemotherapeuticals or antibiotics,corticoids or antihistaminics.But these agents have been found not to be active enough to prevent snoring over long periods,or they led,when taken over the long term, to damage to the nasal and pharyngal mucous membrane. This applies also to the tests made earlier using etheric oils such as for example menthol, camomile,eucalyptus oil etc., in higher concentration.

Only recently has it been possible to show that obstructions which may be regarded as the cause of the snoring, are formed especially by the drying out of the mucous membranes or additional mucous areas with microfissures due to the deposit of tough mucus etc.

European patent application, No. 005 3754(and the equivalent U.S. Pat. No. 4,556,557) from the same applicant describes an agent for combatting snoring which contains a surfactant substance, a stabilizer and a substance which softens the mucous membranes in physiological saline. This agent is to prevent the drying out of the mucous membranes during the night.To attain this it is necessary to infuse a certain amount of the agent into the nose-pharynx cavities before going to sleep.

The object of this invention is to make available an agent for combatting snoring,with which even stubborn cases of snoring can be prevented, but without the appearance of damaging side effects due to adverse influences on the nasal and pharyngal mucous membranes. Especially the noise of snoring during "common snoring" is to be suppressed.

This object is solved according to the invention by an antisnoring agent which contains an active content of a secretolytically and/or secretoproductively active substance together with the usual mucous membrane-compatible carriers and/or thinning agents,and which is suitable for oral administration as well as introduction into the nose-pharyngal cavities. Preferred is an agent with an active dose of a secretolytic substance. The oral administration of the agent according to the invention is especially preferred.

The inventive oral antisnoring agent is distinguished by a potent content of an active ingredient which excites the function of the mucous membrane glands of the respiratory tract with usual carriers or thinning agents.

Further the invention comprises a process for the use of the inventive antisnoring agent.

It is especially advantageous when the inventively used secretolytic drug has the following properties:
(a) regulation and normalization of the mucus viscosity,
(b) reduction of mucus adhesion by the activation of endogenous surfactant properties of the secretion,
(c) stimulation of the serous mucus production and
(d) activation of the operation of the mucoceliary function.

According to the invention, suitable secretolytic drugs are known in the prior art. These known drugs are used in the treatment of illnesses of the respiratory tract, which are accompanied by pathologically altered secretion and applied in the form of tablets etc. or which are administered orally as juices.

According to the invention it has now been found surprisingly that by the use of suitable secretolytic drugs, the snoring which is not an illness but is as described above, i.e. a troublesome phenomenon for other people, can be prevented or reduced. The preferred orally administered secretolytic drugs lead to a stimulation of the mucous membrane glands in the respiratory tract,whereby a liquefaction of tough mucus in the nasal and pharyngal cavity and/or a stimulation of the mucus secretion is caused, which prevents the drying out of the mucous membranes and the formation of microfissures.But also by the infusion or use of a spray device the inventive agent can be applied to the mucous membrane of the nasal/pharyngal cavities.

It is partially absorbed by the latter, so that both because of the absorbed secretolytic substance and due to the effect of the moistening of the nasal/pharyngal mucous membrane it becomes effective. The secretolytic drug absorbed by the nasal and pharyngal mucous membrane causes a stimulation of the mucous membrane glands,whereby the result is a liquefaction of tough mucus which covers the mucous membrane, and/or it leads to a stimulation of the mucus secretion, whereby the drying out of the mucous membranes and the formation of microfissures therein are prevented.

Among the known secretolytic drugs which are suitable according to the invention are inter alia the compounds bromohexin, ambroxol,eprazinon, carbocistin, N-acetyl-L-cystein as well as saponines which are contained e.g. in radix senegae,radix saponariae and radix liquiritiae, as well as substances containing carbohydrates made from radix altae,lichen Islandicus, folia Malvae or carrageen with special preference for bromohexin and ambroxol.

The above agents can be used as such or in the form of their pharmaceutically compatible salts.

The antisnoring agent according to the invention can be administered in various galenic forms.Specially preferred are,for long-term activity, tablets, capsules,-coated tablets,compressed tablets,granulates,microcapsules etc. But it is also possible to administer the oral antisnoring agent in the form of drops or as a juice.

For local application, it is preferably formulated in drops,as a spray or as an ihhalation solution.

The total dose,to be administered to a snorer,of the active ingredient depends on the respective efficiency of the active substance used as well as on the form of application and is in general within the range between 5 and 500 mg,the preference being for between 10 and 100 mg.This dose should be contained in an amount of from 0.5 to 2 ml of the inventive agent, preferably from 0.5 to 1.0 ml.

In the case of the administration of ambroxol,the especially preferred range is a dose of active ingredient of from 30–100, with preference for from 50 to 100 mg. Tests using 30–60 mg ambroxol-HCl produced excellent long-term effects in suppressing snoring.Using bromohexin the preferred range of the active drug is 8–30 mg.Using carbocistin in a dose of 200–400 mg is preferably chosen.

To achieve a long-term effect lasting through the night it is advisable to formulate the inventive antisnoring agent in the retard form.For this purpose the active ingredient must be formulated with adjuvant substances so that it is only released very slowly, which can be effected e.g. by embedding it in a very slowly dissolving matrix. Moreover it is possible to form the active ingredient with adjuvants to make tablets,pellets,granulates or any spheroid particles or compressed tablets, which are then coated with a suitable covering which causes a slow release of the active ingredient in the stomach and/or intestinal tract. From the galenic viewpoint,the active ingredient for retard form should be formulated so that there is no change in the resorption speed in the resorptive part of the stomach-intestinal tract. In many cases it has been found that the active ingredient should be mixed with an emulsifier and optionally coated with an acid-insoluble coating,so that the active ingredient is released in the intestinal juices in solubilized form.

In addition it is possible to administer a two-phase preparation in which e.g. a coated tablet containing 60 mg of ambroxol-HCl has an insulated core of 30 mg ambrox-HC, which is only freed after 3 to 4 hours, while the coating dissolves at once.

To the extent that the above secretolytic drugs are resorbed in the stomach or intestinal tract in inadequate quantities it is recommended that the active ingredient should be used in a mixture with resorption-increasing substances which positively influence the pH .

Such a gale formulation is selected e.g. when using bromohexin. It is advantageous to mix the active ingredient with an acid or an acidic substance in the form of granules, tablet cores, microcapsules etc.To do this, 1 mol of active ingredient is mixed with 1 to 60 moles preferably 5 to 30 moles,of acid or of the acidic substance. Such formulations are described in detail in DE-A 31 26 703 to which we expressly refer.It is preferable to pour the preparations containing the active ingredient into hard gelatine capsules,whose decomposition and thus resorption of the active ingredient take place in intestinal tract. Therefore the secretolytic drugs are in a form which is surrounded by an acid-insoluble but intestinal-juice soluble coating.Especially suitable substances of this type are described in the DE-A No. 31 26 703 named above,to which we refer here. Special mention is made of: methacrylic acid methacryl-acid-ester mixed polymerisate,hydroxypropyl-methyl-cellulosephthalate or celluloseacetatesuccinate.

The measure of surrounding the preparation containing the active ingredient with an acid-insoluble but intestinal-juice soluble coating or a corresponding hard gelatine capsule is especially suitable for making retard forms.

In this way the partially very good solubility of the invention's secretolytic drugs is taken into account,and only slowly are they released in this manner.This method can achieve the presence of the secretolytic drug for some hours in dissolved and resorption-capable form.

The retard forms of the secretolytic broxohexin and ambroxol on the market, known by the tradenames bisolvon and mucosolvan,are especially suitable as antisnoring agents according to the invention.

The preparation of non-retarding tablets,coated tablets, etc. is done by processes known per se. Specially advantageous is administration of microcapsules surrounded by a coating layer, since the breakdown of the active dose takes place into many hundreds of independent small retard forms and thereby an even release of the active agent is ensured.

Preferably mucous membrane-compatible additives,-which can increase the effect of the active substance or otherwise have a favorable effect on the nasal/pharyngal mucous membrane or which protect the inventive antisnoring agent from contamination, are added to the galenic formulations for local use, apart from the active ingredient.

The invention provides that a preservative agent may be added to the local antisnoring agent.By the presence of a preservative,especially after its entry into use and long storage, the antisnoring agent can be protected against microbacterial impurities.

It is especially preferred when the added preservative, which must be mucous membrane-compatible,can take effect via a function for the prevention of microbial growth in the antisnoring agent as a bactericide and/or fungicide on the mucous membranes of the nose/-pharynx cavities.

To the extent that the preservative used as mucous membrane -compatible does not have this effect or only acts to an inadequate extent, it is advisable to add to the agent a suitable substance acting as a mucous membrane disinfectant bactericidally and/or fungicidally on the nasal and pharyngal mucous membranes.

As the preservative in the local antisnoring agents according to the invention,all the preservatives generally used in pharmaceutical preparations can be used,-which prevent microbial growth and do not irritate the mucous membranes of the nasal and pharyngal cavities.-Suitable preservatives are e.g. ethanol,esters of p-hydroxy benzoic acid,2-phenoxyethanol,benzoic acid and its salts, sorbic acid and its esters etc.

Suitable mucous membrane disinfectants which may act both as disinfectants as well as antiseptic drugs include acridine and quinoline derivatives, quaternary ammonium compounds as well as compounds with amidine structures.

Especially good results were obtained according to the invention by an additive of benzalconium chloride,-which is a mild,mucous membrane-compatible disinfectant. This substance impedes any possible rapid new obstruction in that it wards off irritation due to impurities of the nasal mucous membrane and thereby reduces it. Fast and excessive mucus formation would again -in connection with drying possibilities of the mucus - initiate prematurely the snoring process.

Apart from the named benzalconium chloride,other quaternary amines, to the extent that they are not incompatible with mucous membrane, are suitable as the disinfectants in the agents of the invention.

The use of benzododecinium has also been found suitable as a further mucous membrane disinfectant.The addition of chlorobutanol, a compound which has both bactericide as well as fungistatic properties, is suitable as the fungistatically active agent.

The preservatives are added to the agents of the invention for local use, optionally together with bactericide or fungicide substances, in a concentration of from 0.1 to 4% based on the total weight of the agent. Preferably the amount of the concentration of bactericide and/or fungistatic compounds is from 1 to 5 mg based on 1000 ml of the agent of the invention.

Moreover the inventive agent for local use contains substances which exert a smoothing or softening effect on the nasal and pharyngal mucous membranes.

The object of this softening substance is to prevent or reduce the microfissures in the mucous membrane.

For this the polyalcohols are e.g. suitable which prevent the surface drying of the mucous membrane and moreover reduce the surface tension of the water phase. Suitable polyalcohols include ethylene glycol, diethylene glycol, propylene glycol, dipropylene glycol, glycerol, diglycerine, sorbitol, while glycerine and sorbitol are especially suitable.

Moreover the use of panthenol has also been found advantageous for smoothing the mucous membranes. It is mucous membrane-compatible and has an effect similar to that of pantothenic acid. Panthenol also has a regenerating surface effect on the mucous membranes.

These substances(s) for softening or smoothing the mucous membranes are present in the inventive agents in a concentration of from 0.1 to 3% by weight based on the total weight of the agent. The preferred concentration range is from 0.2 to 1.0% by weight.

Mucous membrane-compatible substances which prevent the formation of microfissures or favor the removal of or dissolution of disturbing substances can also be added to the agents of the invention. In this sense it is advantageous to add to the inventive agent a mucous-membrane-compatible enzyme preparation which promotes the dissolution of the disturbing substances. In particular hydrolytic enzymes, lipases, and proteases are suitable as the enzymes. It is preferable to use enzyme preparations which have at least approximately their optimal pH value in the pH range to be found on the nasal and pharyngal mucous membranes, and which under these conditions are as stable as possible.

Moreover to the inventive antisnoring agent for local use, apart from the active ingredient, which is secretolytic in effect, etheric oils as well as mixtures thereof can be added. Especially preferred is the use of ol.thymi, ol.anisi, ol.eucalypti, ol.camomille, ol.menthae, and ol.terebinthiniae. Further the antisnoring agent for local use can contain substances which support the secretolytic effect of the active ingredient or which otherwise have a favorable effect on the properties of the nasal-pharyngal mucous membrane. Especially vitamin A and vitamin E should be named. The presence of vitamin A is found successful due to its regenerative influence on tissue formations, while vitamin E counters all kinds of degeneration, detoxifies, raises the resistance and regenerates the mesenchymal area, which causes a vegetative tonus increase. In the case of addition of vitamin A to the inventive antisnoring agent, the amount used is from about 15000 to 30000 IE/ml. Vitamin E can be added e.g. as acetate to the inventive agent in an amount of ca. 20-200 mg/ml.

Special preparation forms of the inventive antisnoring agent for oral and local use are listed below. The prescriptions below represent some preferred examples from the abundance of possible formulations; they serve to explain the invention, without limiting its scope.

FORMULATION 1

The following composition is prepared for the production of capsules:

| | |
|---|---|
| ambroxol-hydrochloride | 10.0 g |
| maize starch (dry) | 24.0 g |
| aerosil 200 | 0.4 g |

The contents are mixed, passed through a 0.75 mm screen, and poured into about 200 hard gelatine capsules with a capsule filling weight of 170 mg.

FORMULATION 2

Tablets of the following composition were prepared: 1 tablet contains:

| | |
|---|---|
| Carbocistin | 300 mg |
| lactose | 50.0 mg |
| Maize starch | 50.0 mg |
| polyvinylpyrrolidon | 2.0 mg |
| magnesium stearate | 1.0 mg |

The active agent is mixed with lactose and maize starch moistened with an aqueous PVP solution, the mixture is passed through a screen of 1.5 mm and the granulate is dried. After admixture of the lubricant the tablets are pressed.

FORMULATION 3

To prepare an oral antisnoring agent in retard form the following pellets were prepared:

First pellets are prepared, using alcoholic polyvinylpyrrolidon solution, tartaric acid, talc and the active ingredient bromohexin, with about 0.8 mm diameter which contain ca. 20% of bromohexin and about 75% of tartaric acid.

The above dried pellets are then sprayed in a coating pan with a solution of methacrylic acid-methacrylcc acid ester-mixed polymer(acid val.200-300) and hydroxypropylmethylcellulosephthalate in isopropanol-/acetate in a ratio of pellet to coating of 10:1, wherein as the softener triacetin is used.

FORMULATION 4

The following solution for infusion in the nose is prepared(0.5 to 1 ml per nostril):

| | |
|---|---|
| ambroxol-HCl | 10.0 g |
| glycerine | 1.0 ml |
| benzalconium chloride | 1.0 g |
| physiological saline up to 100 ml. | |

FORMULATION 5

Drops with the following composition were prepared:

| | |
|---|---|
| bromohexin | 1.2 g |
| glycerol | 1.0 ml |
| chlorobutanol | 1.0 g |
| ol.camomille | 0.2 g |
| physiological saline up to 100 g. | |

To prevent snoring respectively 0.5 to 1 ml are infused in each nostril.

The invention further comprises a process for local application of the inventive agent for combatting snoring which consists of the fact that the agent is applied in adequate amount to the nasal and pharyngal mucous membranes by means of a suitable device. To achieve the effect desired, relatively small quantities of the inventive agent are enough, amounting to from ca. 0.2 to 2 ml. Preferably the inventive agent is applied in an amount of from 0.5 to 1.0 in the nose and pharynx area. For this purpose the agent according to the invention is introduced by infusion or by spraying into each nostril using a suitable device or a suitable instrument, so that the liquid is applied to the nasal and pharyngal mucous membranes. Suitable devices for the performance of the process are known. For example the agent can be applied by an aerosol device, by an atomizer, a rinsing pipette or by pipette flasks containing the agent. The agent is used in the evening before going to sleep, either when lying or standing, but preferably with head tilted backwards. If this is necessary, the use can be repeated during the night.

The tests of the agent according to the invention which have been made on human beings have shown that it does not cause any incompatibilities, not even when taken over longer periods, because the components in the cited concentrations are not toxic and are already used in rhinology as such.

I claim:

1. The method for substantially reducing or eliminating snoring in humans, comprising the step of orally administering to humans afflicted with snoring, a composition containing a therapeutically effective amount of ambroxol in a dose of from 30 to 100 mg in a suitable carrier.

2. The method for substantially reducing or eliminating snoring in humans, comprising the step of topically applying to the nasopharyngeal mucous membranes of humans afflicted with snoring, a composition comrising a therapeutically effective amount of ambroxol in a dose of from 30 to 100 mg in a suitable carrier.

* * * * *